United States Patent [19]

Lange et al.

[11] Patent Number: 4,459,297
[45] Date of Patent: Jul. 10, 1984

[54] OXADIAZINEDIONES, THEIR PREPARATION, AND THEIR USE FOR THE CONTROL OF INSECTS AND ARACHNIDS

[75] Inventors: Arno Lange, Mannheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 456,116

[22] Filed: Jan. 6, 1983

[30] Foreign Application Priority Data

Jan. 7, 1982 [DE] Fed. Rep. of Germany ....... 3200196

[51] Int. Cl.³ .................... A01N 43/72; C07D 273/04
[52] U.S. Cl. ......................... 424/248.58; 424/248.54; 544/67
[58] Field of Search ..................... 544/67; 424/248.58, 424/248.54

[56] References Cited

U.S. PATENT DOCUMENTS 4,150,158 4/1979 Huff ............................... 424/248.57
4,348,394 9/1982 Sirrenberg et al. ............ 424/248.57

FOREIGN PATENT DOCUMENTS 2732115 1/1978 Fed. Rep. of Germany .
2905687 8/1979 Fed. Rep. of Germany .

*Primary Examiner*—Richard Raymond
*Attorney, Agent, or Firm*—Keil & Weinkauf

[57] ABSTRACT

Diphenyloxadiazinediones of the formula (I)

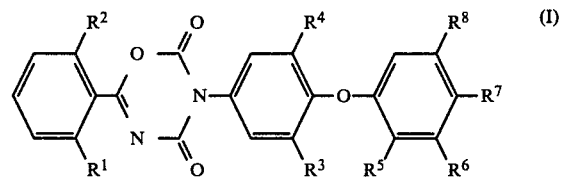

where $R_1$ is $CH_3$, F, Cl or Br, $R_2$ is H, F or Cl and $R_3$ to $R_8$ are H, F, Cl, Br, $CH_3$, $CF_3$, $-OCF_3$, $-OCHF_2$, $OCF_2CHClF$, $-OCH_3$ or $-OC_2H_5$, their preparation and their use, especially as insecticides and acaricides.

4 Claims, No Drawings

OXADIAZINEDIONES, THEIR PREPARATION, AND THEIR USE FOR THE CONTROL OF INSECTS AND ARACHNIDS

The present invention relates to novel oxadiazinediones, processes for their preparation, and insecticides and acaricides containing these compounds as active ingredients.

German Laid-Open Applications DOS Nos. 2,905,687 and 2,732,115 have disclosed that oxadiazinediones have an insecticidal action.

We have found that oxadiazinediones (I)

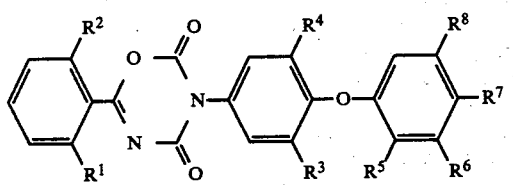

where $R^1$ is $CH_3$, F, Cl or Br, $R^2$ is H, F or Cl and $R^3$ to $R^8$ are H, F, Cl, Br, $CH_3$, $CF_3$, $-OCF_3$, $-OCHF_2$, $-OCF_2CHClF$, $-OCH_3$ or $-OC_2H_5$, have a particularly powerful insecticidal and acaricidal action.

Compounds where $R^1$ and $R^2$ are F, or $R^1$ and $R^2$ are Cl, or $R^1$ is Cl and $R^2$ is F, or $R^1$ is Cl and $R^2$ is H are preferred.

The following combinations of substituents $R^3$ to $R^8$ are preferred:

(a) If $R^3$ and $R^4$ are chlorine or bromine, not less than three of the radicals $R^5$ to $R^8$ are hydrogen, and one may be halogen;

(b) if $R^3$ is hydrogen and $R^4$ is F, Cl, Br or $CF_3$, not less than two of the radicals $R^3$ to $R^8$ are hydrogen, and one or more is F, Cl, Br, $CF_3$, $OCF_3$ or $OCHF_2$;

(c) if $R^3$ and $R^4$ are hydrogen, not less than two of the radicals $R^5$ to $R^8$ are F, Br, $OCF_3$ or $OCHF_2$ or one or more is Cl or $CF_3$.

Oxadiazinediones (I) are obtained by reacting a corresponding benzoylisocyanate (II)

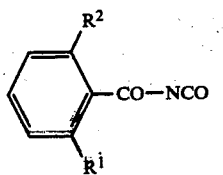

with a corresponding isocyanate (III)

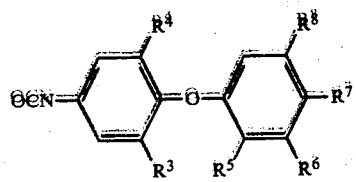

in a conventional manner.

Approximately stoichiometric amounts of the reactants may be used, and the reaction is generally carried out at below 160° C., preferably at from 80° to 120° C. An effective amount of a catalyst, eg. triethylamine or a tin compound, such as dibutyl-tin diacetate, is advantageously added.

Side reactions of the isocyanates may be prevented by an inhibitor, eg. phosphorus trichloride.

In cases where a solvent is to be used, suitable solvents are substances which are chemically inert under the reaction conditions, eg. aliphatic and aromatic hydrocarbons, which may be chlorinated or nitrated, such as benzene, toluene, xylenes, gasoline, chlorobenzenes, 1,2-dichloroethane, methylene chloride, chloroform, nitromethane and carbon tetrachloride, cyclic and acyclic ethers, such as diethyl ether, dibutyl ether, tetrahydrofuran and dioxane, acyclic and cyclic ketones, such as acetone, methyl ethyl ketone, methyl isopropyl ketone and cyclohexanone, and nitriles, such as acetonitrile and benzonitrile, and mixtures thereof.

The reaction generally proceeds under atmospheric pressure and can be carried out batchwise or continuously. The yield is virtually quantitative.

The oxadiazinediones (I) are obtained in solid form, and as a rule are sufficiently pure for the intended purpose. If necessary, they may be purified by recrystallization or washing with a solvent, such as ether, petroleum ether, cyclohexane or toluene. They are characterized by elementary analysis and their melting point and IR and NMR spectra.

The benzoyl isocyanates (II) can be prepared, for example, in accordance with the instructions in J. Org. Chem. 28 (1963), 1805–1811 or J. Agr. Food Chem. 21 (1973), 348.

It is also possible to prepare the phenyl isocyanates by known methods (cf., eg., Weygand-Hilgetag, Organisch-Chemische Experimentierkunst, 1970 or German Laid-Open Application DOS No. 2,538,178). The information provided by, for example, Barry et al, Pr. Irish Acad. 53 B, 61, 66, 82 (1950) may be referred to for the preparation of the diphenyl ethers.

PREPARATION EXAMPLE (a) 9.2 g of 2,6-difluorobenzoyl isocyanate and 14.0 g of 3-chloro-4-(4-chlorophenoxy)phenyl isocyanate were stirred with 3 drops of triethylamine at 100° C. for 5 hours. The product was washed thoroughly with petroleum ether and dried. 16 g of 2-(2,6-difluorophenyl)-5-[3-chloro-4-(4-chlorophenoxy)phenyl], 4H-5,6-dihydro-1,3,5-oxadiazine-4,6-dione of melting point 180°–185° C. were obtained (corresponding to No. 1 in the table which follows).

(b) 4.76 g of 2,6-difluorobenzoyl isocyanate and 6.27 g of 4-(3-trifluoromethylphenoxy)phenyl isocyanate were stirred with 0.2 ml of $PCl_3$ at 70° C. for 2½ hours and at 110° C. for 2 hours. 11 g of 2-(2,6-difluorophenyl)-5-[4-(3-trifluoromethylphenoxy)phenyl]-4H-5,6-dihydro-1,3,5-oxadiazine-4,6-dione were obtained. The compound was washed with ether and recrystallized from toluene/cyclohexane, after which it had a melting point of 127°–129° C.

(c) 3.66 g of 2,6-difluorobenzoyl isocyanate, 5.8 g of 4-(4-bromophenoxy)phenyl isocyanate and 2 drops of dibutyl-tin diacetate were stirred at 50° C. for 2 hours, at 100° C. for 4 hours at 120° C. for 8 hours. 9 g of 2-(2,6-difluorophenyl)-5-[4-(4-bromophenoxy)phenyl]-4H-5,6-dihydro-1,3,5-oxadiazine-4,6-dione were obtained. The compound was washed with ether, after which it had a melting point of 186°–188° C.

The substances given, together with their melting points, in Table 1 which follows were obtained in accordance with the above preparation instructions. The numbers 1 and 2 in the table relate to Preparation Examples (a) and (c) respectively.

Other typical compounds as classified in Table 2 can be obtained, and they may be expected to be effective on the basis of their structural similarity with the substances investigated.

TABLE 1

| No. | $R^1$ | $R^2$ | $R^3$ | $R^4$ | $R^5$ | $R^6$ | $R^7$ | $R^8$ | M.p. |
|---|---|---|---|---|---|---|---|---|---|
| 1 | F | F | H | Cl | H | H | Cl | H | 180–185 |
| 2 | F | F | H | H | H | H | Br | H | 186–188 |
| 3 | Cl | Cl | H | Cl | H | H | Cl | H | 196–199 |
| 4 | Br | H | H | Cl | H | H | Cl | H | 185–187 |
| 5 | $CH_3$ | H | H | Cl | H | H | Cl | H | 165–168 |
| 6 | Cl | Cl | H | H | H | H | Br | H | 191–193 |
| 7 | F | F | H | Cl | H | H | $OCHF_2$ | H | 169–173 |
| 8 | Cl | Cl | H | Cl | H | H | $OCHF_2$ | H | 200–204 |
| 9 | F | F | H | H | H | H | $OCHF_2$ | H | 185–187 |
| 10 | Cl | H | H | H | H | H | $OCHF_2$ | H | 179–182 |
| 11 | Cl | Cl | Cl | H | H | H | H | Cl | 174–177 |
| 12 | F | F | H | H | H | H | Cl | H | 194–196 |
| 13 | Cl | Cl | H | H | H | H | Cl | H | 192–193 |
| 14 | Cl | H | H | H | H | H | Cl | H | 181–182 |
| 15 | F | Cl | H | Cl | H | H | Cl | H | 175–180 |
| 16 | Cl | H | H | Cl | H | H | Cl | H | 127–134 |
| 17 | Cl | H | H | H | H | H | Br | H | 183–184 |
| 18 | Cl | Cl | H | H | H | H | $OCHF_2$ | H | 192–195 |
| 19 | F | F | H | F | H | H | Br | H | 189–193 |
| 20 | Cl | Cl | H | H | H | $CF_3$ | H | H | 170–172 |
| 21 | F | F | H | H | Cl | H | Cl | H | 183–185 |
| 22 | Cl | Cl | H | H | Cl | H | Cl | H | 206–208 |
| 23 | Cl | H | H | H | Cl | H | Cl | H | 182–183 |

TABLE 2

| No. | $R^1$ | $R^2$ | $R^3$ | $R^4$ | $R^5$ | $R^6$ | $R^7$ | $R^8$ |
|---|---|---|---|---|---|---|---|---|
| 24 | F | F | H | H | H | H | $CF_3$ | H |
| 25 | Cl | H | H | Cl | H | H | $OCHF_2$ | H |
| 26 | Cl | Cl | H | F | H | H | Br | H |
| 27 | Cl | H | H | H | H | $CF_3$ | H | H |
| 28 | F | F | Cl | H | H | H | H | Cl |
| 29 | Cl | H | Cl | H | H | H | H | Cl |
| 30 | F | F | H | Cl | H | H | H | H |
| 31 | F | F | H | Cl | H | H | F | H |
| 32 | Cl | Cl | H | Cl | H | H | F | H |
| 33 | F | Cl | H | H | H | H | Br | H |
| 34 | F | Cl | H | Cl | H | H | $OCHF_2$ | H |
| 35 | F | Cl | H | H | H | H | $OCHF_2$ | H |
| 36 | F | F | H | Cl | H | H | $CF_3$ | H |
| 37 | F | F | H | Cl | H | H | $OCF_3$ | H |
| 38 | F | F | H | Cl | H | H | $OCH_3$ | H |
| 39 | F | F | H | F | H | H | Cl | H |
| 40 | Cl | Cl | H | F | H | H | Cl | H |
| 41 | F | Cl | H | F | H | H | Cl | H |
| 42 | Cl | H | H | F | H | H | Cl | H |
| 43 | F | Cl | H | F | H | H | Br | H |
| 44 | Cl | H | H | F | H | H | Br | H |
| 45 | Br | H | H | F | H | H | Br | H |
| 46 | $CH_3$ | H | H | F | H | H | Br | H |
| 47 | Cl | H | H | F | H | H | $CF_3$ | H |
| 48 | F | F | H | F | H | H | $OCF_3$ | H |
| 49 | F | F | H | F | H | H | $OCH_3$ | H |
| 50 | F | F | H | H | H | H | $C_3$ | H |
| 51 | Cl | H | H | F | H | H | $OC_2H_5$ | H |
| 52 | F | F | H | H | H | H | $OCF_2CHClF$ | H |
| 53 | Cl | H | Cl | Cl | H | H | F | H |
| 54 | F | F | Cl | Cl | H | H | Cl | H |
| 55 | F | F | Cl | Cl | H | H | H | H |
| 56 | Cl | Cl | Cl | Cl | H | H | H | H |
| 57 | F | Cl | Cl | Cl | H | H | H | H |
| 58 | Cl | H | Cl | Cl | H | H | H | H |
| 59 | F | F | Br | Br | H | H | H | H |
| 60 | F | F | Br | H | H | H | Cl | H |
| 61 | F | F | $CF_3$ | H | H | H | Cl | H |
| 62 | Cl | Cl | $CF_3$ | H | H | H | Cl | H |
| 63 | F | Cl | $CF_3$ | H | H | H | Cl | H |
| 64 | Cl | H | $CF_3$ | H | H | H | Cl | H |
| 65 | F | H | $CH_3$ | H | H | H | Cl | H |
| 66 | F | Cl | H | H | H | $CF_3$ | H | H |
| 67 | F | F | H | H | H | Cl | H | H |
| 68 | F | Cl | Cl | H | H | H | H | Cl |
| 69 | F | Cl | H | H | Cl | H | Cl | H |
| 70 | F | F | H | H | Cl | H | $CF_3$ | H |

TABLE 2-continued

| No. | $R^1$ | $R^2$ | $R^3$ | $R^4$ | $R^5$ | $R^6$ | $R^7$ | $R^8$ |
|---|---|---|---|---|---|---|---|---|
| 71 | F | Cl | H | H | H | H | Cl | H |

The diphenyloxadiazinediones of the formula I, and agents prepared with them, are suitable for effectively combating pests particularly from the classes of insects and Arachnida. They may be used as pesticides for crop protection, and in the hygiene, stores protection and veterinary sector.

Examples of injurious insects from the Lepidoptera order are Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia, pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae, and Aporia crataegi;

examples from the Coleoptera order are Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies, abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus, and Blastophagus piniperda;

examples from the Diptera order are Lycoria pectoralis, Mayetiola destructor, Dasyneura brassicae, Contarinia tritici, Haplodiploosis equestris, Tipula paludosa, Tipula oleracea, Dacus cucurbitae, Dacus Oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata, and Hypoderma lineata;

examples from the Hymenoptera order are Athalia rosae, Hoplocampa minuta, Monomorium pharaonis, Solenopsis geminata, and Atta sexdens;

examples from the Heteroptera order are Nezara viridula, Eurygaster integriceps, Blissus leucopterus, Dysdercus cingulatus, Dysdercus intermedius, Piesma quadrata, and Lygus pratensis;

examples from the Homoptera order are Perkinsiella saccharicida, Nilaparvata lugens, Empoasca fabae, Psylla mali, Psylla piri, Trialeurodes vaporariorum, Aphis fabae,

*Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

The agents may also be used for combating members of the Arachnida class, such as *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus,* and of the Nemathelminthes class, such as root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dust and broadcasting agents may be prepared by mixing or grinding the active ingredients with a solid carrier.

Examples of formulations are given below.

I. 5 parts by weight compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

IV. 20 parts by weight of compound no. 13 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

V. 80 parts by weight of compound no. 19 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient.

In the open, application rates are from 0.2 to 10, and preferably from 0.5 to 2.0, kg of active ingredient per hectare.

There may be added to the individual active ingredients (if desired, immediately before use (tankmix) oils of various types, herbicides, fungicides, other pesticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropane carboxylate, (s)-alpha-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,transchrysanthemate, 2-methyl-5-(2-propynyl)-3-furylmethyl-chrysanthemate, and alpha-cyano-3-phenoxybenzyl-alpha-isopropyl-4-chlorophenylacetate.

Application Examples

The compounds used for the following experiments were compound 1 from Table 1 and, for comparison purposes, 2-(2,6-difluorophenyl)-5-(3,4-dichlorophenyl)-4H,5,6-dihydro-1,3,5-oxadiazine-4,6-dione (disclosed in German Laid Open Application DE-OS 27 32 115).

It was also able to be shown that the compound according to the invention has an action on mosquito larvae which is significantly better than of a typical commercially available benzoylurea derivative, diflubenzofuron.

1. Breeding experiment with houseflies (*Musca domestica*)

4.5 ml of skimmed milk was introduced into 50 ml penicillin flasks, and 0.5 ml of the aqueous active ingredient formulation was then added. After brief mixing, a ball of absorbent cotton was introduced and about 50 housefly larvae placed on it. The flasks were covered and kept at room temperature. The development was assessed after 7 days.

| Results | | |
|---|---|---|
| Compound 1 | 2.5 ppm | 100% kill |
| Comparative agent | 50.0 ppm | 100% kill |
| | 25.0 ppm | 60% kill |

2. Breeding experiment with mosquito larvae (*Aedes aegypti*)

Formulations of the active ingredients were added to 200 ml of tapwater; 20 to 30 mosquito larvae of the 3rd to 4th larval stage were then introduced.

The vessels were kept at 25° C. Pupation and hatching of the imagoes, which took place after 10 to 12 days, was monitored. During the observation period, a powdered food for tropical fish was fed once.

| Results | | |
|---|---|---|
| Compound 1 | 0.001 ppm | 100% kill |
| Comparative agent | 0.25 ppm | 100% kill |
| | 0.01 ppm | ineffective |
| Diflubenzofuron | 0.004 ppm | 100% kill |
| | 0.002 ppm | 60% kill |
| | 0.001 ppm | 20% kill |

3. Breeding experiment with cotton stainers (*Dysdercus intermedius*)

Cotton stainers (*Dysdercus intermedius*) in the 4th larval stage were exposed for 24 hours to a layer of the candidate compounds in Petri dishes 10 cm in diameter.

The survivors were then kept in 1 liter jars on moist quartz sand (to which active ingredient solutions had been added) until the F₁ generation hatched.

In the treatment,
2.5 mg/dish was equivalent to 25 ppm in the sand;
1.0 mg/dish was equivalent to 10 ppm in the sand;
0.5 mg/dish was equivalent to 5 ppm in the sand; etc.
Mortality and multiplication were assessed.

| Results | | |
|---|---|---|
| Compound 1 | 25 ppm | 100% kill |
| Comparative agent | 25 ppm | ineffective. |

4. Action on spider mites (*Tetranychus telarius*)

Potted bushbeans which had developed the first pair of true leaves and were under heavy attack from spider mites (*Tetranychus telarius*) were sprayed to runoff from all sides in a spray cabinet with 50 ml of aqueous formulations of the active ingredients.

The plants were investigated after 8 days for signs of living mites.

| Results | | |
|---|---|---|
| Compound 1 | 0.05% | 100% kill |
| Comparative agent | 0.1% | 60% kill |

We claim:

1. A diphenyloxadiazinedione of the formula

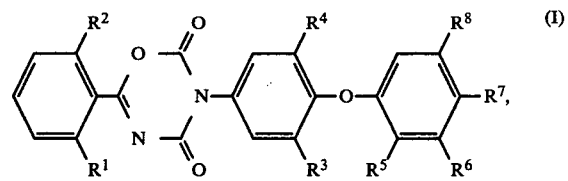

where $R^1$ is $CH_3$, F, Cl or Br, $R^2$ is H, F or Cl and $R^3$ to $R^8$ are H, F, Cl, Br, $CH_3$, $CF_3$, $-OCF_3$, $-OCHF_2$, $-OCF_2CHClF$, $-OCH_3$ or $-OC_2H_5$.

2. A process for manufacturing oxadiazinediones as claimed in claim 1, wherein a benzoyl isocyanate of the formula

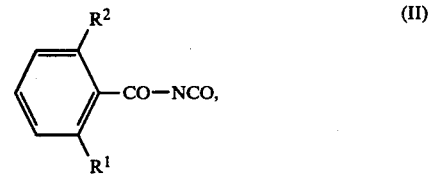

where $R^1$ and $R^2$ have the meanings given in claim 1, is reacted with an isocyanate of the formula

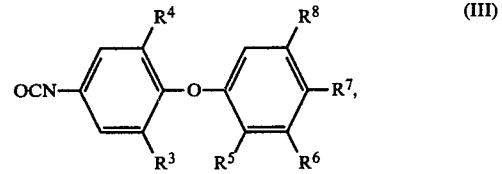

where $R^3$ to $R^8$ have the meanings given in claim 1, at a sufficiently high temperature below 160° C.

3. An insecticidal and acaricidal agent which comprises an inert carrier and an effective amount of an oxadiazinedione of the formula I of claim 1.

4. A process for combating insects and Arachnida, wherein an effective amount of an oxadiazinedione of the formula I of claim 1 is allowed to act on the insects or Arachnida, and/or their habitat.

* * * * *